US010839067B2

(12) United States Patent
Cannariato et al.

(10) Patent No.: US 10,839,067 B2
(45) Date of Patent: Nov. 17, 2020

(54) ACTIVE CONTROL OF ANONYMOUS FORUM FOR MEMBERS OF SERVICE

(71) Applicant: TTM PTP, Inc., Astoria, NY (US)

(72) Inventors: Robyn Cannariato, Jamaica, NY (US); Christopher Hetherington, Bayside, NY (US); Dennis Ostermann, East Rockaway, NY (US); William Yeack, New York, NY (US)

(73) Assignee: TTM PTP, INC., Astoria, NY (US)

( * ) Notice: Subject to any disclaimer, the term of this patent is extended or adjusted under 35 U.S.C. 154(b) by 257 days.

(21) Appl. No.: 16/054,726

(22) Filed: Aug. 3, 2018

(65) Prior Publication Data

US 2019/0057208 A1 Feb. 21, 2019

Related U.S. Application Data

(60) Provisional application No. 62/546,897, filed on Aug. 17, 2017.

(51) Int. Cl.
| | | |
|---|---|---|
| *G06F 21/40* | (2013.01) |
| *H04L 9/32* | (2006.01) |
| *G16H 20/70* | (2018.01) |
| *H04L 29/06* | (2006.01) |
| *G16H 10/60* | (2018.01) |

(Continued)

(52) U.S. Cl.
CPC ............ *G06F 21/40* (2013.01); *G06F 21/335* (2013.01); *G16H 10/60* (2018.01); *G16H 20/70* (2018.01); *G16H 40/63* (2018.01); *G16H 40/67* (2018.01); *G16H 50/70* (2018.01); *G16H 80/00* (2018.01); *H04L 9/3213* (2013.01); *H04L 63/0407* (2013.01); *H04L 63/102* (2013.01); *H04L 63/104* (2013.01); *H04L 65/4007* (2013.01); *H04L 2209/42* (2013.01)

(58) Field of Classification Search
CPC ........ G06F 21/40; G16H 10/60; G16H 50/70; G16H 20/70; H04L 63/0407; H04L 63/104; H04L 9/3213; H04L 63/102; H04L 65/4007; H04L 2209/42; H06F 21/335; H16H 80/00; H16H 40/67
USPC .......................................................... 726/2
See application file for complete search history.

(56) References Cited

U.S. PATENT DOCUMENTS

| | | | |
|---|---|---|---|
| 2007/0067405 A1 | 3/2007 | Eliovson | |
| 2008/0045192 A1* | 2/2008 | Zhao ..................... H04L 63/104 | |
| | | | 455/414.2 |
| 2017/0250980 A1* | 8/2017 | Mehta ..................... H04L 63/06 |

* cited by examiner

*Primary Examiner* — Brandon S Hoffman
*Assistant Examiner* — Nega Woldemariam
(74) *Attorney, Agent, or Firm* — Intelletek Law Group, PLLC; Gabriel Daniel, Esq.

(57) ABSTRACT

A method and system of providing emotional health support resources to a member of a service (MOS) are provided. A data packet is received from a user device of a user. A group identification (ID) is extracted from the data packet. The group ID is sent to an authentication server for authentication. Upon not receiving a token from the authentication server, the user is blocked from support resources of a private network. Upon receiving a token from the authentications server, the user is identified as an anonymous authorized member of service (MOS). Information is interactively requested and received from the anonymous MOS. One or more support resources of the private network are identified based on the received information from the anonymous MOS. Access is provided to the one or more support resources of the private network via the user device.

18 Claims, 4 Drawing Sheets

(51) Int. Cl.
   *G16H 50/70* (2018.01)
   *G06F 21/33* (2013.01)
   *G16H 80/00* (2018.01)
   *G16H 40/67* (2018.01)
   *G16H 40/63* (2018.01)

ACTIVE CONTROL OF ANONYMOUS FORUM FOR MEMBERS OF SERVICE

CROSS REFERENCE TO RELATED APPLICATIONS

The present application claims the benefit of priority under 35 U.S.C. § 119 from U.S. Provisional Patent Application Ser. No. 62/546,897, entitled "Active Control of Anonymous Forum for Members of Service," filed on Aug. 17, 2017, which is hereby incorporated by reference in their entirety for all purposes.

BACKGROUND

Technical Field

The present disclosure generally relates to networked devices, and more particularly, to allowing members of service, anonymous access to network resources via their networked devices.

Description of the Related Art

Much like war veterans, police officers experience stress on a daily basis, and are at risk of developing post-traumatic stress disorder. Police officers can be exposed to more traumas in a single tour than most civilians experience in a lifetime, and, unlike military personnel, are not segregated from civilians and given extended time and resources to enable reintroduction into society. To the contrary, police officers often deal with society and its traumas on an ongoing basis. Left unattended, the tension and stress that result from being barraged by these traumas on a daily basis can have devastating effects. The results can include difficulties with personal relationships, alcoholism, suicidal thoughts, and unintentional overreactions in policing. In today's society, external forces have amplified criticism of police work, resulting in a national crisis in policing. Many believe that the trend toward adversarial relationship between police and the community should be reversed at the earliest.

One way of addressing the stresses faced by police officers and fire fighters, collectively referred to herein as members of service (MOS), is via social counseling. However, many MOS are shy to express their needs and concerns, out of fear of being identified, ridiculed, or sidelined. It is within these considerations and others that this application has been written.

SUMMARY

According to various exemplary embodiments, a computing device, a non-transitory computer readable storage medium, and a method of providing emotional health support resources to a member of a service (MOS) are provided. A data packet is received from a user device of a user. A group identification (ID) is extracted from the data packet. The group ID is sent to an authentication server for authentication. Upon not receiving a token from the authentication server, the user is blocked from support resources of a private network. Upon receiving a token from the authentications server, the user is identified as an anonymous authorized member of service (MOS). Information is interactively requested and received from the anonymous MOS. One or more support resources of the private network are identified based on the received information from the anonymous MOS. Access is provided to the one or more support resources of the private network via the user device.

In one embodiment, sending the group ID to the authentication server for authentication includes facilitating multi-factor authentication between the user device and the authentication server.

In various embodiments, the MOS is at least one of (i) a police officer, (ii) a fire fighter, and (iii) a soldier returning from a tour of duty.

In one embodiment, identifying one or more support resources of the private network based on the received information from the anonymous MOS, includes determining an emotional health condition of the anonymous MOS based on the received information from the anonymous MOS. One or more support resources of the private network are identified based on the determined emotional health condition.

In one embodiment, identifying one or more support resources of the private network based on the received information from the anonymous MOS further includes, upon determining that a threshold number of anonymous MOS have a substantially similar emotional health condition, organizing a virtual meeting for each of the anonymous MOS having the substantially similar emotional health condition.

In one embodiment, a new data packet is received from the user device for an appointment. The token is extracted from the new data packet. It is determined whether the user is authorized to use the private network based on the extracted token. If so, the user is identified as an anonymous authorized member of service (MOS) and allowed to hold the appointment via the user device.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps.

DETAILED DESCRIPTION

Overview

Figure 1:
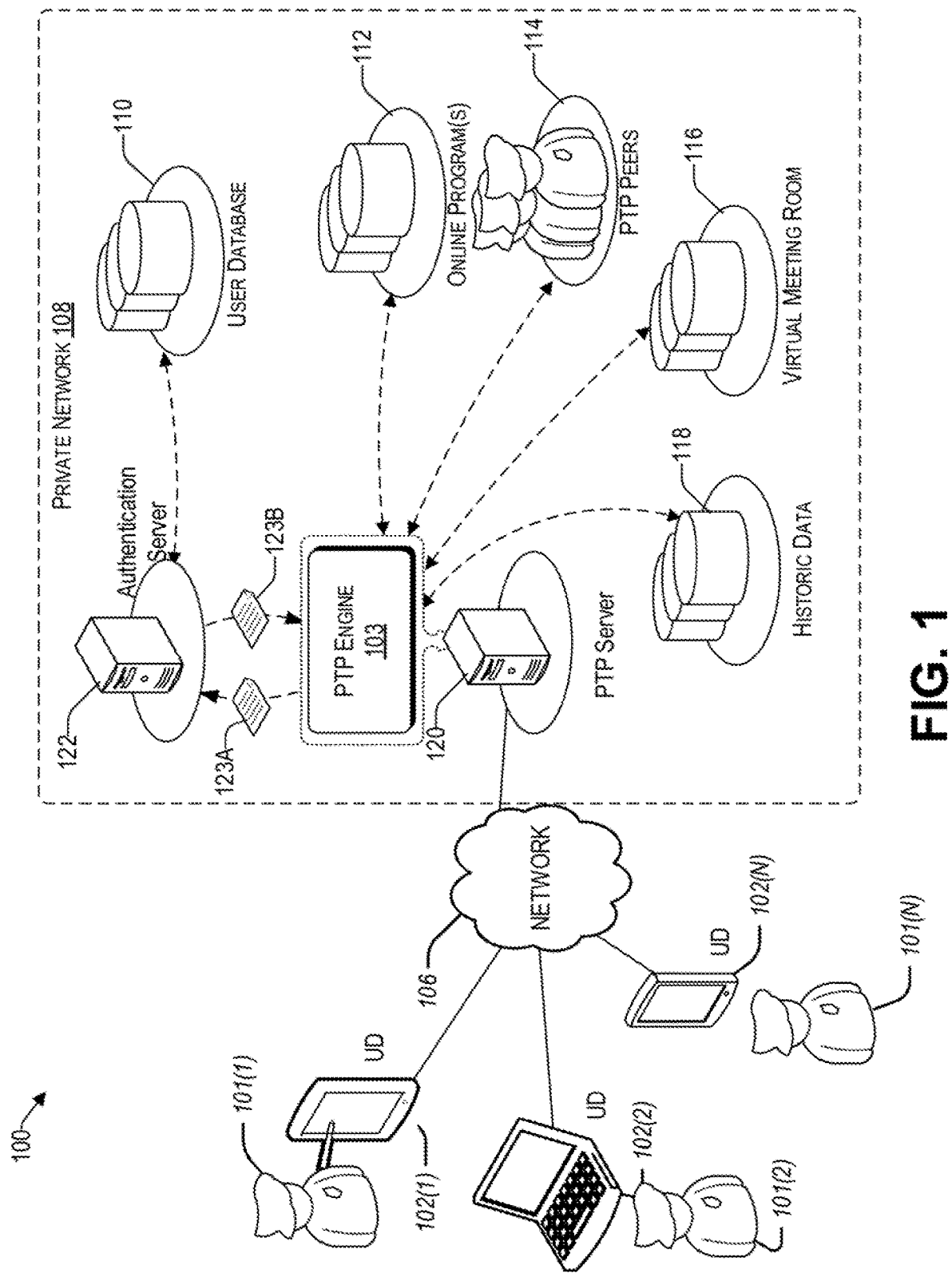
FIG. 1 illustrates an example architecture for implementing a system for providing online resources to members of service, anonymously.

In the following detailed description, numerous specific details are set forth by way of examples to provide a thorough understanding of the relevant teachings. However, it should be apparent that the present teachings may be practiced without such details. In other instances, wellknown methods, procedures, components, and/or circuitry have been described at a relatively high-level, without detail, to avoid unnecessarily obscuring aspects of the present teachings.

The present disclosure relates to allowing MOS anonymous access to online resources to a private network, via networked user devices of the anonymous MOS to provide relief from effects of stress during their service. Such stress may have a cumulative effect. For example, police officers may eventually be impacted by ongoing daily stress experienced during their daily service. What is described herein is a computerized post-tour processing (PTP) system that is configured to diminish the stress of MOS individually and/or in a virtual group setting.

For example, informal daily post-tour sessions can quickly become a comfortable part of the daily law enforcement routine, nearly identical to the pre-tour roll call. One difference between the two is that, unlike roll call, where officers are listening to instructions about what they will do during the day, in the post-tour session officers may be telling their PTP peer(s) what they actually did during that day in an anonymous setting without worry of being identified. Such session can accomplish several benefits. First, it can provide a level of positive peer support with regard to the performance and behavior of police officers. Second, it can encourage community among police officers. These effects are salient not only because of their positive impact, but also because of the resulting ease of acceptance of the program among police officers; rather than being a dreaded inquisition at the end of a tour, the post-tour sessions actually can become "de rigueur" and welcome. In one embodiment, the post-tour processing may provide real-time, regular monitoring of the mental health of all participating officers, and as such serve as an informal early warning system of elevated stress in police officers, for which intervention can be administered long before that stress could manifest itself in unfavorable performance or behavior with the public.

Post-tour processing sessions may be provided by PTP peers. For example, PTP peers may be MOS from the department they are serving; at the discretion of the municipality, they may be personnel with precinct duties, they may be from the returning tour, or there may be a more efficient solution depending on the circumstances of the department. The PTP peer may be an MOS who has volunteered for the PTP peer role, and has subsequently been accepted and trained by a predetermined group (e.g., Talk to Me Post Tour Processing (TTM PTP)). This enables the PTP peer to have genuine empathy for the difficulties that his or her fellow law enforcement officers face on a daily basis, and also provides the PTP peer with an essential credibility on the part of fellow law enforcement officers.

Applicants have identified that it is important to the success of PTP systems and other programs offered to MOS, that confidentiality be maintained. In this way, MOS are free to discuss their concerns that may have been experienced during the day. To that end, the infrastructure described herein keeps the MOS anonymous from the virtual resources of the PTP environment.

Example Architecture

FIG. 1 illustrates an example architecture 100 for implementing a system for providing online resources to a member of service anonymously. Architecture 100 includes a network 106 that allows various user devices 102(1) to 102(n) to communicate with each other, as well as any other components that are connected to the network 106, such as a PTP server 120, authentication server 122, online program(s) 112 PTP peers 114, virtual meeting rooms 116, historical data repository 118, etc.

The network 106 may be, without limitation, a local area network ("LAN"), a virtual private network ("VPN"), a cellular network, the Internet, or a combination thereof. For example, the network 106 may include a mobile network that is communicatively coupled to a private network 108 that provides various ancillary services, such as communication with online program(s) 112 PTP peers, virtual meeting rooms 116, and the like, as well as the Internet. To facilitate the present discussion, network 106 will be described, by way of example only and not by way of limitation, as a mobile network as may be operated by a carrier or service provider to provide a wide range of mobile communication services and supplemental services or features to its subscriber customers and associated mobile device users.

The network 106 allows a PTP engine 103, sometimes referred to herein as a support engine, running on the PTP server 120 to communicate with one or more users 101(1) to 101(n), sometimes referred to herein as members of service (MOS), over their user devices (UD's) 102(1) to 102(n), respectively, to request a resource from the private network 108, such as access to an online program 112 or to a virtual meeting room 116 to address stress associated with their service.

For purposes of later discussion, several user devices appear in the drawing, to represent some examples of the devices that may be used to initiate an IT request via the network 106. Today, user devices typically take the form of portable handsets, smart-phones, tablet computers, personal digital assistants (PDAs), virtual reality (VR) devices, augmented reality (AR) devices, and smart watches, although they may be implemented in other form factors, including consumer, and business electronic devices. A user device (e.g., 102(1)) may be used to interact with the private network 108 over the network 106, to receive one or more support resources provided by the private network 108, including anonymous interaction with the services provided thereby.

In one embodiment, the private network 108 includes a PTP engine 103 that runs on a PTP server 120, a user database 110, and online program(s) 112 database. The PTP engine 103 is operative to receive requests from MOS 101(1) to 101(N) via their user devices 102(1) to 102(N), respectively. The PTP engine 103 is configured to provide access to authorized MOS while maintaining anonymity. To that end, in one embodiment, the PTP server 120 does not store individual MOS identity. Rather, it operates with tokens that are received from an authentication server 122 that is operative to determine whether a MOS is authorized to use the services of the private network 108 and provide a token, which may be randomized, for that MOS, thereby cloaking the identity of the user.

For example, at the end of a tour of duty, a MOS (e.g., 101(1)) may want to interact with the PTP resources of the private network 108, for example, to unwind and reduce stress. To that end, the MOS 101(1) contacts the PTP server 120 via the network 106. While the PTP server provides anonymity to individual users, it does not allow unauthorized access. To remain anonymous, the user device 102(1) provides a data packet to the PTP server 120, which indicates that the MOS is authorized to use the PTP resources of the private network 108 while remaining anonymous. In various scenarios, the MOS 101(1) may want to start a new session or continue an ongoing interaction with the resources of the private network 108. For a new session, the data packet of the user device 102(1) may include a group user identification (UID), which may be common for the MOS 102(1) to 102(N). For example, all NY police officers may have the same group UID. Upon receiving the group UID, the PTP engine 103 extracts the group UID and sends the credentials (i.e., group UID) 123A of the user to the authentication server 122 to determine whether the user is authorized to use the services of the private network 108. In one embodiment, upon confirmation of the group UID, the authentication server may generate a (e.g., random) token for the MOS which is provided 123B to the PTP engine 103 to be forwarded to the user device 102(1) of the MOS 101(1). This token may be used by the MOS 101(1) for subsequent interactions with the private network 108, together with the group ID, to continue a session under a same alias profile under the token. Receipt of the token by the PTP server (either from the authentication server 122 or the user device 102(1) is indicative that the user is a MOS and authorized to access the resources of the private network 108.

In other embodiments, the authentication server may use multi-factor authentication (MFA) prior to providing access to the resources of the private network 108. To that end, the authentication server 122 requests additional information from the MOS 101(1) either directly with the user device 102(1) or bridged by the PTP server 120. In various embodiments, MFA may include a personal identification number (PIN) of the MOS, biometric information, equipment identifier (e.g., international mobile station equipment identity (IMEI) mobile identification number (MIN), mobile equipment identifier (MEID), or the like), etc. In one embodiment, the MFA data received from the MOS 101(1) via their user device 102(1) is compared to user information stored in a user database 110. It is emphasized that while in some embodiments the authentication server 122 can identify the identity of the user, the identity is not provided to the PTP server or other support resources of the private network 108, such as online program(s) 112, PTP peers 114, or virtual meeting room(s) 116, thereby assuring the anonymity of the MOS.

Upon authentication, the PTP engine 103 interacts with the MOS 101(1) via their user device 102(1) to determine what support resources of the private network 108 are appropriate. In various embodiments, the interaction may be in the form of a written questionnaire displayed on the user device 102(1) or via voice prompts. The MOS 102(1) can respond by filling out the interactive questionnaire via text or via voice prompts, which, in various embodiments, are converted to text via voice recognition either at the user device 102(1) or by the PTP engine 103.

In one embodiment, a user interface of the user device of the MOS indicates whether the identity of the MOS is cloaked. For example, during interaction with the authentication server 122, the user interface may indicate that the user identity is not cloaked. For example, a red frame around the screen, a message displayed on the screen, an audible background tone, and/or haptic feedback may be provided by the user device to alert the MOS that their identity may not be cloaked presently. In contrast, during the questionnaire portion, where the identity of the MOS is cloaked, the privacy is indicated on the user interface of the user device (e.g., green border around the screen, audio/visual messages indicating security, and/or a more soothing background music). In this way, an environment is created that is more conducive for the MOS to communicate freely.

Based on the content of the user input, the appropriate one or more support services of the private network 108 are provided. For example, the PTP engine 103 may identify the emotional health condition of the MOS based on the series of interactive questions between the MOS and the PTP engine 103. Based on the response received from the MOS, the PTP engine 103 may identify one or more online programs 112 (e.g., multimedia, such as voice and/or video) that may be available immediately for the MOS to use.

Accordingly, based on the symptom(s) (sometimes referred to herein as emotional health condition) identified by the PTP engine 103, a PTP peer 114 may be assigned to the anonymous MOS. Depending on the emotional health condition, a PTP peer who is most qualified to deal with the symptom/situation may be selected by the PTP engine 103. If the selected PTP peer is not immediately available, the PTP engine can set up an appointment between the anonymous MOS 101(1) and the PTP peer 114. The MOS 101(1) can later attend the virtual appointment (i.e., to an event, such as a class, seminar, group session, presentation of media, etc.,) over the network 106 by using the same random token provided by the authentication server 122. It should be noted that if the random token is lost by the MOS 101(1), then the PTP engine 103 cannot accommodate the appointment because the true identity of the MOS is cloaked.

In some embodiments, machine learning is used to construct algorithms that can learn from and make predictions based on the content of the user input and historical data provided by a historical database 118. The historical data may relate to prior emotional health conditions of MOS that were successfully handled by the resources of the private network 108, which now acts as a corpus of data to learn from by the PTP engine and develop algorithms. Such algorithms operate by building a model from stored prior inputs or baselines therefrom in order to make data-driven predictions or decisions and/or to provide threshold conditions to indicate an emotional health condition of the MOS, and/or treatment of the MOS, rather than following strictly static criteria.

In one embodiment, upon the PTP engine 103 determining that a threshold number of MOS that have substantially similar symptom is above a predetermined threshold, then the PTP engine 103 can organize a virtual meeting room 116 where several MOS (e.g., 101(1) to 101(N)) can anonymously participate for a group session at a predetermined time. Similarly, if the PTP engine 103 determines that the severity of the condition is above a predetermined threshold, then the availability of the resources may be escalated (e.g., the resources of the private network 108 are prioritized to the subject MOS over less severe cases). Again, the interested MOS can later keep their appointment by logging in using a combination of their group UID and their corresponding random token previously provided by the authentication server 122.

In one embodiment, return online visits to appointments do not need the group UID; rather, the random token provided by the authentication server 122 is sufficient. In various embodiments, upon receipt of the random token, the PTP engine 103 may compare the random token to a table of tokens stored in a memory of the PTP server or request authentication from the authentication server 122 by sending the token to the authentication server 122 and receiving confirmation therefrom. Upon the PTP engine 103 determining that the MOS is authorized to hold the appointment, the PTP engine 103 provides access to the resource of the private network 108 (e.g., PTP Peer 114 or online program 112.

By virtue of the architecture 100 discussed herein, the PTP engine 103 of the PTP server 120 can automatically determine whether an anonymous MOS is authorized to use the private network 108 and organize the appropriate support resources therefor, thereby providing an anonymous infrastructure that improves the well-being of each MOS using the services described herein.

Example User Device

Figure 2:
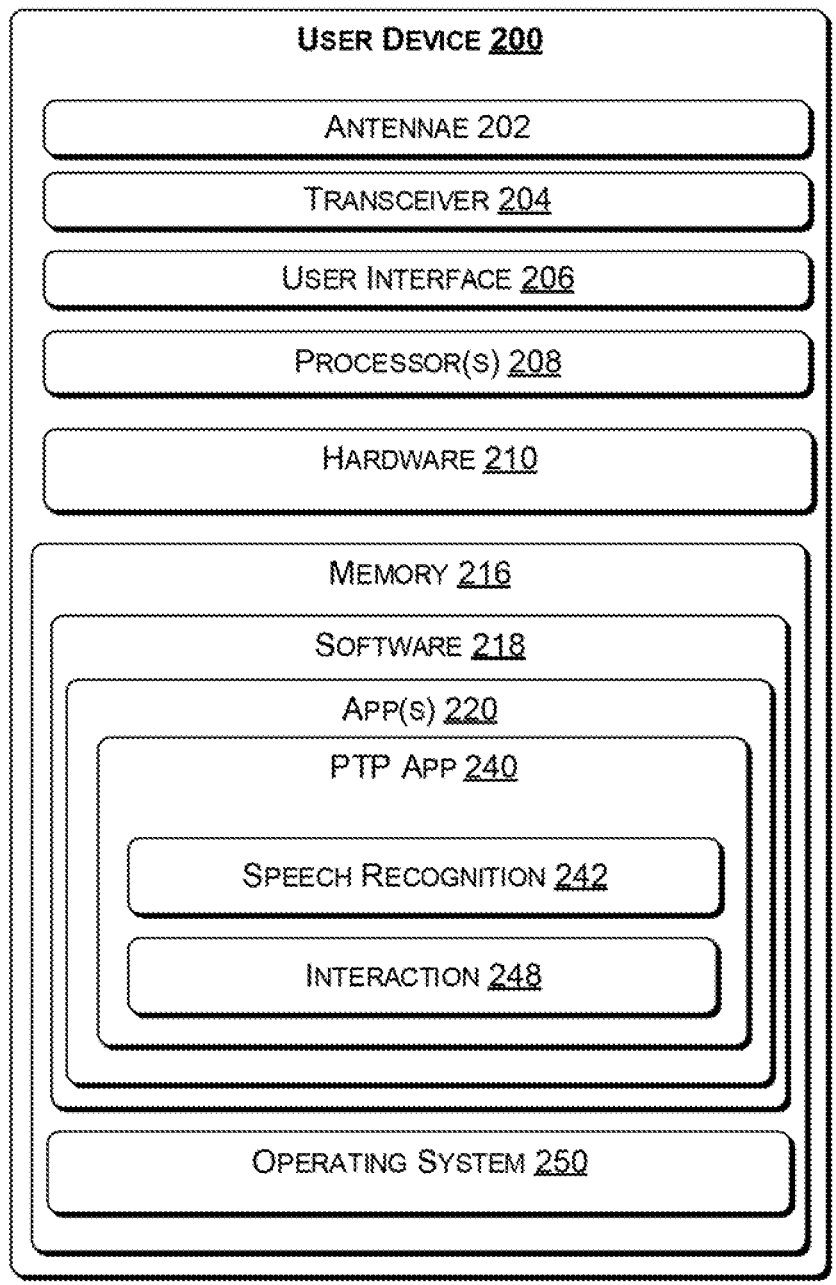
FIG. 2 illustrates a block diagram showing various components of an illustrative user device at a high level.

As discussed in the context of FIG. 1, the system for providing online resources to members of service in the architecture 100 may involve different types of user devices. To that end, FIG. 2 illustrates a block diagram showing various components of an illustrative user device 200 at a high level. For discussion purposes, the illustration shows the user device 200 in the form of a wireless computing device.

The user device 200 may include one or more antennae 202; a transceiver 204 for cellular, Wi-Fi communication, and/or wired communication; a user interface 206; one or more processors 208; hardware 210; and memory 216. In some embodiments, the antennae 202 may include an uplink antenna that sends radio signals to a base station, and a downlink antenna that receives radio signals from the base station. In some other embodiments, a single antenna may both send and receive radio signals. The same or other antennas may be used for Wi-Fi communication. These signals may be processed by the transceiver 204, sometimes collectively referred to as a network interface, which is configured to receive and transmit digital data. In one embodiment, the user device 200 does not include an antenna 202 and communication with external components is via wired communication.

In one embodiment, the user device 200 includes a user interface 206 that enables a user to provide input and receive output from the user device 200. For example, the user interface 206 may include a data output device (e.g., visual display, audio speakers, haptic device, etc.,) that may be used to provide notifications from the PTP engine 103 of the PTP server 120. The user interface 206 may also be used to receive information from the support services of the private network 108 of FIG. 1.

The user interface 206 may also include one or more data input devices. The data input devices may include, but are not limited to, combinations of one or more of keypads, keyboards, mouse devices, touch screens, microphones, speech recognition packages, and any other suitable devices or other electronic/software selection interfaces. For example, the data input devices may be used by a user to enter requests for support services from the private network 108 during a communication session between the user device 200 and the PTP engine 103.

The user device 200 may include one or more processors 208, which may be a single-core processor, a multi-core processor, a complex instruction set computing (CISC) processor, or another type of processor.

The hardware 210 may include a power source and digital signal processors (DSPs), which may include single-core or multiple-core processors. The hardware 210 may also include network processors that manage high-speed communication interfaces, including communication interfaces that interact with peripheral components. The network processors and the peripheral components may be linked by switching fabric. The hardware 210 may further include hardware decoders and encoders, a network interface controller, and/or a USB controller. In some embodiments, the hardware 210 includes biometric sensor devices, such as fingerprint, voice, face, etc., which are converted into an electrical signal representing the identity of the user.

The memory 216 may be implemented using computer-readable media, such as computer storage media. Storage media includes volatile and non-volatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD), high definition video storage disks, or other optical storage, magnetic cassettes, magnetic tape, magnetic disk storage or other magnetic storage devices, or any other non-transmission medium that can be used to store information for access by a computing device.

The memory 216 may store various software components or modules that are executable or accessible by the processor(s) 208 and controller(s) of the user device 200. The various components of the memory 216 may include software 218 and an operating system 250. The software 218 may include various applications 220. The software 218 may also include a PTP application 240 having several modules. Each module may include routines, program instructions, objects, and/or data structures that perform tasks or implement abstract data types.

For example, the PTP application 240 of the user device 200 may include a speech recognition module 242 that enables the recognition (and possible translation) of spoken language into text, such that it can be further processed by the PTP engine 103. There may be an interaction application 248 operative to interact with the PTP engine 103 to make communication with the authentication server 122 and/or online program(s) 112, PTP peers 114, and virtual meeting room 116 possible. In one embodiment, the interaction engine 248 stores the random token provided by the authentication server 122 such that a session can be continued with that token at a later date.

The operating system 250 may include components that enable the user device 200 to receive and transmit data via various interfaces (e.g., user controls, communication interface, and/or memory input/output devices), as well as process data using the processor(s) 208 to generate output. The operating system 250 may include a presentation component that presents the output (e.g., display the data on an electronic display of the user device 200, store the data in memory 216, transmit the data to another electronic device, etc.). Additionally, the operating system 250 may include other components that perform various additional functions generally associated with an operating system 250.

Example Process

Figure 3:
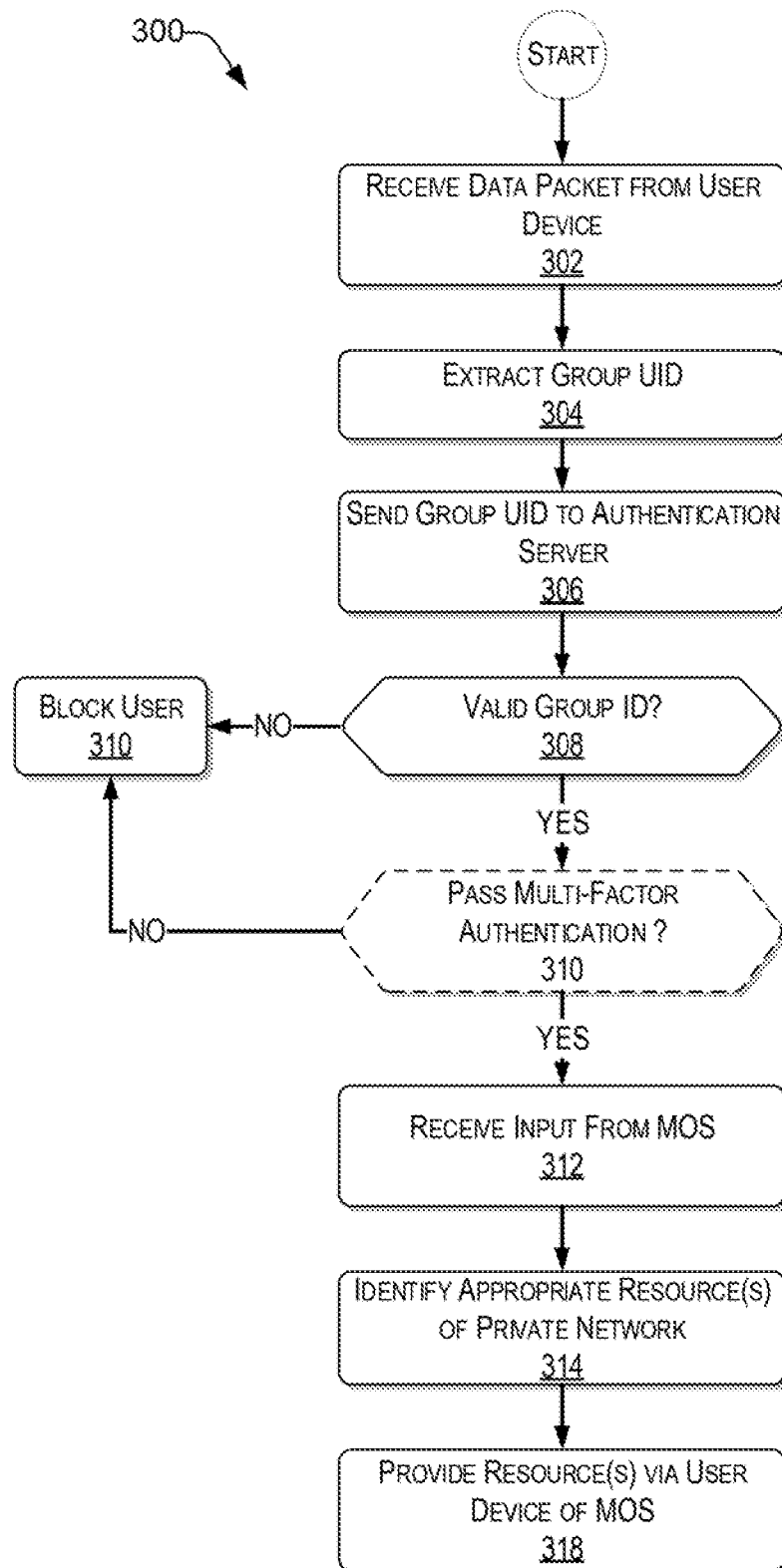
FIG. 3 presents an illustrative process of providing access to services of a post-tour processing system to a member of a service, anonymously.

With the foregoing overview of the architecture 100 and example user device 200, it may be helpful now to consider a high-level discussion of an example process. To that end, FIG. 3 presents an illustrative process 300 of providing access to services of a post-tour processing system to a member of a service, anonymously. Process 300 is illustrated as a collection of blocks in a logical flowchart, which represents a sequence of operations that can be implemented in hardware, software, or a combination thereof. In the context of software, the blocks represent computer-executable instructions that, when executed by one or more processors, perform the recited operations. Generally, computer-executable instructions may include routines, programs, objects, components, data structures, and the like that perform functions or implement abstract data types. The order in which the operations are described is not intended to be construed as a limitation, and any number of the described blocks can be combined in any order and/or performed in parallel to implement the process. For discussion purposes, the process 300 is described with reference to the architecture 100 of FIG. 1.

At block 302, the PTP engine 103 (running on the PTP server 120) receives a data packet from a user device 102(1), over a network 106. The user 101(1) of the user device 102(1), sometimes referred to herein as a member of a service, may be subscribed to a service or be part of an organization that provides a private network 108 that includes emotional health support resources for its members. For example, the request may be in the context of accessing a support service of the private network 108. The data packet of the user device 102(1) may include a group UID, which authorizes the MOS to the services discussed herein.

At block 304 the PTP engine 103 extracts the group UID from the data packet and sends it to the authentication server 122 for authentication (i.e., block 306).

At block 308, it is determined whether the group ID is valid to indicate that the user is an MOS who is authorized to use the support services of the private network 108. In one embodiment, such validation is provided by receiving a (e.g., randomized) token from the authentication server 122 in response to sending the group UID thereto. In some embodiments, the authentication server performs multi-factor authentication (MFA). To that end, the authentication server 122 requests additional information from the MOS 101(1) either directly with the user device 102(1) or bridged by the PTP server 120. In one embodiment, the MFA data received from the MOS 101(1) via their user device 102(1) is compared to user information stored in a user database 110. Upon determining that a valid group ID is not provided (i.e., "NO" at decision block 308), the PTP engine 103 blocks the user from accessing the support services of the private network 108. Similarly, upon determining that multi-factor authentication has not been passed (i.e., NO" at decision block 310), the PTP engine 103 blocks the user from accessing the support services of the private network 108.

However, upon validation (i.e., "YES" at decision block 308 (and 310)), the process continues with block 312, where information is solicited from the MOS via their user device 102(1). As discussed previously, the interaction may be in the form of a written questionnaire displayed on the user device 102(1) or via voice prompts. In various embodiments, the questions may be a predetermined list of questions or follow a question tree. For example, by using a question tree, different types of questions are asked based on an answer to a prior question, thereby leading to a better understanding of the emotional health condition of the MOS.

At block 314, based on the content of the user information, the appropriate one or more support services of the private network 108 are identified. For example, there may be one or more appropriate online programs 112, a PTP peer 114, or an existing group session. In one embodiment, the appropriate resources are identified by an algorithm of the PTP engine that has been trained by machine learning based on historical data provided by a historical database 118.

In some embodiments, the PTP engine 103 may create a resource via scheduling using the randomized token as an identifier. The MOS can then log in via a data packet comprising the group UID and their assigned randomized token to access the scheduled resource of the private network 108 (i.e., block 318). A MOS may become aware of an appointment or a resource upon subsequent login with their randomized token. For example, the user interface may provide recommended forums, meetings, and the like.

Example Computer Platform

Figure 4:
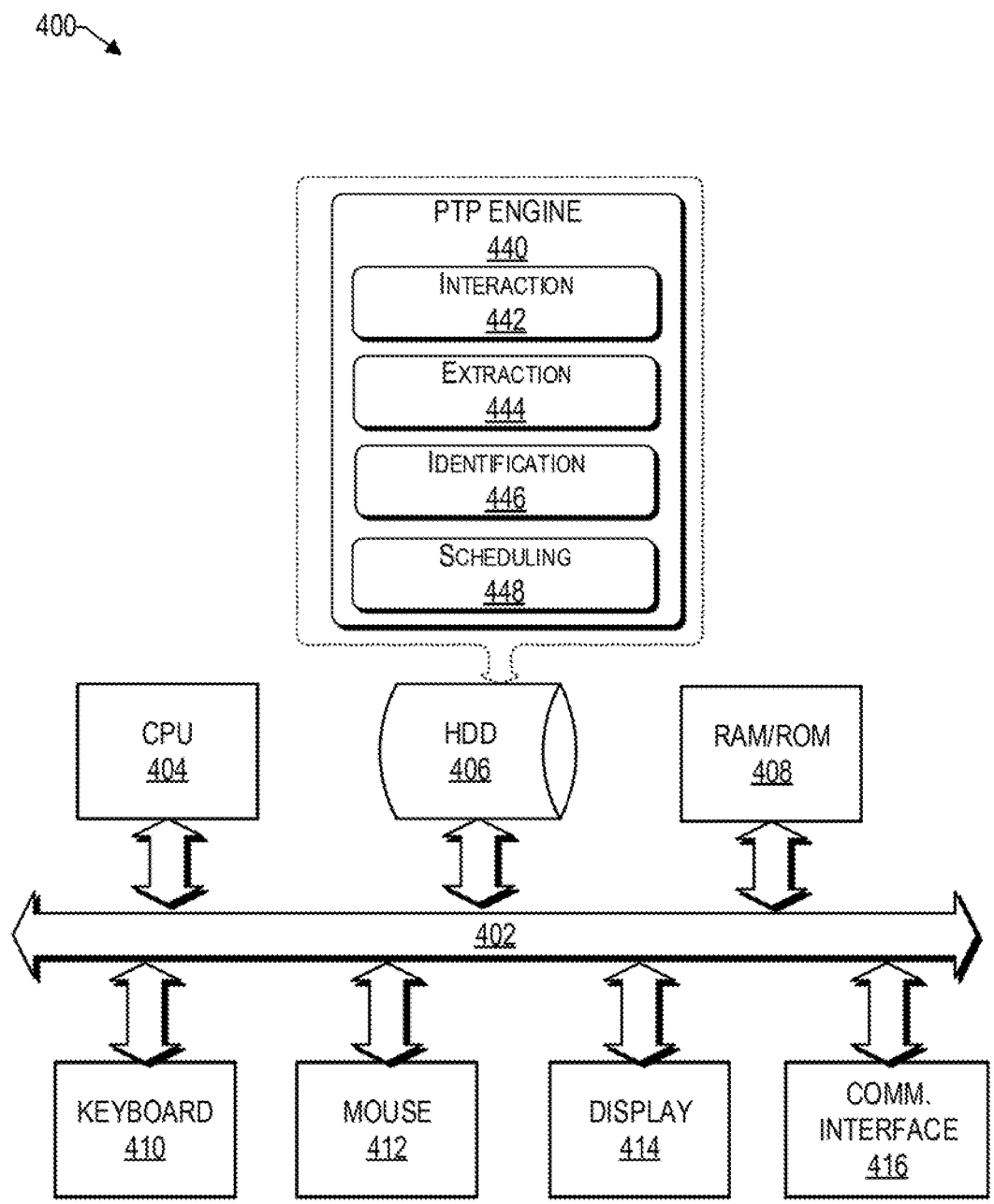
FIG. 4 provides a functional block diagram illustration of a computer hardware platform.

As discussed above, functions relating to providing access to services of a post-tour processing system to a member of a service in an anonymous way, can be performed with the use of one or more computing devices connected for data communication via wireless or wired communication, as shown in FIG. 1 and in accordance with the process 300 of FIG. 3. An exemplary computing device in the form of a user device 200 has been discussed above with respect to FIG. 2. FIG. 4 provides a functional block diagram illustration of a computer hardware platform. In particular, FIG. 4 illustrates a network or host computer platform 400, as may be used to implement a server, such as the PTP server 120 of FIG. 1.

The computer platform 400 may include a central processing unit (CPU) 404, a hard disk drive (HDD) 406, random access memory (RAM) and/or read only memory (ROM) 408, a keyboard 410, a mouse 412, a display 414, and a communication interface 416, which are connected to a system bus 402.

In one embodiment, the HDD 406, has capabilities that include storing a program that can execute various processes, such as the PTP engine 440, in a manner described herein. The PTP engine 440 may have various modules configured to perform different functions.

For example, there may be an interaction module 442 that is operative to receive requests for services of the private network 108 from a user device and to send data to the user device. In one embodiment, the interaction module 442 is operative to indicate to the user device whether the identity of the MOS is cloaked by sending an appropriate data package to the user device over a network, such that the status is indicated on a user interface of the user device, as discussed herein.

In one embodiment, there is an extraction module 444 operative to extract information included in one or more data packets from user devices.

In one embodiment, there is an identification module 446 operative to analyze the information provided by a MOS via their user device to identify one or more appropriate resources of the private network 108. In some embodiments, the identification module 446 can organize/create resources based on meeting demand by a threshold number of MOS having similar symptom(s).

In one embodiment, there is a scheduling module 448 operative to schedule virtual meeting rooms, which can be entered via the predetermined randomized tokens. Stated differently, a MOS who is scheduled to participate in a virtual meeting 116 and/or with a PTP peer 114, can use their assigned randomized token (and/or in combination with a combination with their group ID) to take advantage of the identified service of the private network 108.

Conclusion

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

Aspects of the present disclosure are described herein with reference to a flowchart illustration and/or block diagram of a method, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the FIGS. herein illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

What is claimed is:

1. A computing device comprising:
   a processor;
   a network interface coupled to the processor to enable communication over a network;
   a storage device for content and programming coupled to the processor;
   a post tour engine software stored in the storage device, wherein an execution of the post tour engine by the processor configures the computing device to perform acts comprising:
   receiving a data packet from a user device of a user;
   extracting a group identification (ID) from the data packet;
   sending the group ID to an authentication server for authentication; and
   upon not receiving a token from the authentication server, blocking the user from support resources of a private network;
   upon receiving a token from the authentication server:
      identifying the user as an anonymous authorized member of service (MOS);

interactively requesting and receiving information from the anonymous MOS;
identifying one or more support resources of the private network based on the received information from the anonymous MOS; and
providing access to the one or more support resources of the private network via the user device,
wherein identifying one or more support resources of the private network based on the received information from the anonymous MOS, comprises:
determining an emotional health condition of the anonymous MOS based on the received information from the anonymous MOS; and
identifying one or more support resources of the private network based on the determined emotional health condition.

2. The computing device of claim 1, wherein sending the group ID to the authentication server for authentication comprises: facilitating multi-factor authentication between the user device and the authentication server.

3. The computing device of claim 1, wherein receipt of a token from the authentication server is indicative that the user is an anonymous MOS who has passed multi-factor authentication.

4. The computing device of claim 1, wherein the one or more support resources of the private network include at least one of: (i) an online multimedia program, (ii) an online group session between anonymous MOS, (iii) virtual meeting room for anonymous MOS, (iv) and a peer support MOS.

5. The computing device of claim 1, wherein identifying one or more support resources of the private network based on the received information from the anonymous MOS further comprises: upon determining that a threshold number of anonymous MOS have a substantially similar emotional health condition, organizing a virtual meeting for each of the anonymous MOS having the substantially similar emotional health condition.

6. The computing device of claim 5, wherein a reservation is provided to each of the anonymous MOS to participate in the virtual meeting using each of their tokens as an identifier, respectively.

7. The computing device of claim 1, wherein identifying one or more support resources of the private network based on the received information from the anonymous MOS, comprises:
upon determining that a severity of the emotional health condition of the anonymous MOS is above a predetermined threshold, prioritizing the one or more support resources of the private network for the anonymous MOS.

8. The computing device of claim 1, wherein execution of the post tour engine further configures the computing device to perform acts comprising:
receiving a new data packet from the user device for an appointment;
extracting the token from the new data packet;
determining whether the user is authorized to use the private network based on the extracted token;
upon determining that the user is authorized to use the private network based on the extracted token:
identifying the user as an anonymous authorized member of service (MOS); and
allowing the MOS to hold the appointment via the user device.

9. The computing device of claim 8, wherein determining whether the user is authorized to use the private network based on the extracted token comprises:
sending the token to the authentication server for authentication; and
receiving a confirmation from the authentication server that the user is an authorized anonymous MOS.

10. A non-transitory computer readable storage medium tangibly embodying a computer readable program code having computer readable instructions that, when executed, causes a computing device to carry out a method of providing support resources of a private network, comprising:
receiving a data packet from a user device of a user;
extracting a group identification (ID) from the data packet;
sending the group ID to an authentication server for authentication; and
upon not receiving a token from the authentication server, blocking the user from the support resources of the private network;
upon receiving a token from the authentication server:
identifying the user as an anonymous authorized member of service (MOS);
interactively requesting and receiving information from the anonymous MOS;
identifying one or more support resources of the private network based on the received information from the anonymous MOS; and
providing access to the one or more support resources of the private network via the user device,
wherein identifying one or more support resources of the private network based on the received information from the anonymous MOS, comprises:
determining an emotional health condition of the anonymous MOS based on the received information from the anonymous MOS; and
identifying one or more support resources of the private network based on the determined emotional health condition.

11. The non-transitory computer readable storage medium of claim 10, wherein sending the group ID to the authentication server for authentication comprises: facilitating multi-factor authentication between the user device and the authentication server.

12. The non-transitory computer readable storage medium of claim 10, wherein the MOS is at least one of (i) a police officer, (ii) a fire fighter, and (iii) a soldier returning from a tour of duty.

13. The non-transitory computer readable storage medium of claim 10, wherein the one or more support resources of the private network include at least one of: (i) an online multimedia program, (ii) an online group session between anonymous MOS, (iii) virtual meeting room for anonymous MOS, (iv) and a peer support MOS.

14. The non-transitory computer readable storage medium of claim 10, wherein identifying one or more support resources of the private network based on the received information from the anonymous MOS further comprises:
upon determining that a threshold number of anonymous MOS have a substantially similar emotional health condition, organizing a virtual meeting for each of the anonymous MOS having the substantially similar emotional health condition.

15. The non-transitory computer readable storage medium of claim 10, wherein identifying one or more support resources of the private network based on the received information from the anonymous MOS, comprises:

upon determining that a severity of the emotional health condition of the anonymous MOS is above a predetermined threshold, prioritizing the one or more support resources of the private network for the anonymous MOS.

16. The non-transitory computer readable storage medium of claim 10, further comprising:
receiving a new data packet from the user device for an appointment;
extracting the token from the new data packet;
determining whether the user is authorized to use the private network based on the extracted token;
upon determining that the user is authorized to use the private network based on the extracted token:
identifying the user as an anonymous authorized member of service (MOS); and
allowing the MOS to hold the appointment via the user device.

17. The non-transitory computer readable storage medium of claim 16, wherein determining whether the user is authorized to use the private network based on the extracted token comprises:
sending the token to the authentication server for authentication; and
receiving a confirmation from the authentication server that the user is an authorized anonymous MOS.

18. A computer implemented method of providing emotional health support resources to a member of a service, the method comprising:
receiving a data packet from a user device of a user;
extracting a group identification (ID) from the data packet;
sending the group ID to an authentication server for authentication; and
upon not receiving a token from the authentication server, blocking the user from support resources of a private network;
upon receiving a token from the authentication server:
identifying the user as an anonymous authorized member of service (MOS);
interactively requesting and receiving information from the anonymous MOS;
identifying one or more support resources of the private network based on the received information from the anonymous MOS; and
providing access to the one or more support resources of the private network via the user device,
wherein identifying one or more support resources of the private network based on the received information from the anonymous MOS, comprises:
determining an emotional health condition of the anonymous MOS based on the received information from the anonymous MOS; and
upon determining that a severity of the emotional health condition of the anonymous MOS is above a predetermined threshold, prioritizing the one or more support resources of the private network for the anonymous MOS.

* * * * *